US009452957B2

(12) United States Patent
Senetar et al.

(10) Patent No.: US 9,452,957 B2
(45) Date of Patent: Sep. 27, 2016

(54) OPTIONS TO REDUCE FOULING IN MTO DOWNSTREAM RECOVERY

(71) Applicant: UOP LLC, Des Plaines, IL (US)

(72) Inventors: John J. Senetar, Naperville, IL (US); Joseph A. Montalbano, Bartlett, IL (US); Daniel A. Kauff, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 298 days.

(21) Appl. No.: 14/313,539

(22) Filed: Jun. 24, 2014

(65) Prior Publication Data

US 2015/0368168 A1      Dec. 24, 2015

(51) Int. Cl.

| *C07C 1/20* | (2006.01) |
| *C07C 4/02* | (2006.01) |
| *C07C 7/00* | (2006.01) |
| *C10G 31/06* | (2006.01) |
| *C10G 55/04* | (2006.01) |
| *C10G 75/00* | (2006.01) |
| *C10G 3/00* | (2006.01) |
| *C10G 9/00* | (2006.01) |
| *C10G 21/00* | (2006.01) |

(52) U.S. Cl.
CPC .................. *C07C 7/005* (2013.01); *C07C 1/20* (2013.01); *C10G 3/00* (2013.01); *C10G 9/00* (2013.01); *C10G 21/00* (2013.01); *C10G 31/06* (2013.01); *C10G 55/04* (2013.01); *C10G 75/00* (2013.01)

(58) Field of Classification Search
CPC .............. C07C 1/20; C07C 7/04; C07C 4/02
USPC ................ 585/802, 809, 639, 638, 648, 324
See application file for complete search history.

(56) References Cited

U.S. PATENT DOCUMENTS

| 6,403,854 B1 | 6/2002 | Miller et al. |
| 7,329,790 B2 | 2/2008 | Bjorklund et al. |
| 7,741,528 B2 | 6/2010 | Chang et al. |
| 2004/0079392 A1* | 4/2004 | Kuechler .................. C07C 1/20 134/22.19 |
| 2005/0038304 A1* | 2/2005 | Van Egmond ............ C07C 1/20 585/324 |
| 2009/0005624 A1 | 1/2009 | Bozzano |

FOREIGN PATENT DOCUMENTS

WO         2014/031431 A1      2/2014

OTHER PUBLICATIONS

PCT International Search Report and Written Opinion dated Sep. 3, 2015 for PCT/US201/030301.

* cited by examiner

*Primary Examiner* — Thuan D Dang

(57) ABSTRACT

A process is presented for removing the fouling problems associated with the product recovery in a methanol to olefins conversion process. The process includes passing the quenched MTO process stream to a product separator, wherein an intermediate stream is generated and includes water and heavier hydrocarbons. The intermediate stream is processed to remove the buildup of heavier hydrocarbons.

7 Claims, 2 Drawing Sheets

OPTIONS TO REDUCE FOULING IN MTO DOWNSTREAM RECOVERY

FIELD OF THE INVENTION

The field of the invention relates to the process of converting oxygenates to olefins. In particular, the invention relates to the recovery of a purified olefin stream from the effluent from a methanol to olefins reactor.

BACKGROUND

The use of plastics and rubbers are widespread in today's world. The production of these plastics and rubbers are from the polymerization of monomers which are generally produced from petroleum. The monomers are generated by the breakdown of larger molecules to smaller molecules which can be modified. The monomers are then reacted to generate larger molecules comprising chains of the monomers. An important example of these monomers is light olefins, including ethylene and propylene, which represent a large portion of the worldwide demand in the petrochemical industry. Light olefins, and other monomers, are used in the production of numerous chemical products via polymerization, oligomerization, alkylation and other well-known chemical reactions. Producing large quantities of light olefin material in an economical manner, therefore, is a focus in the petrochemical industry. These monomers are essential building blocks for the modern petrochemical and chemical industries. The main source for these materials in present day refining is the steam cracking of petroleum feeds.

With the increase in demand, other sources for monomers are providing for an increase in supply while becoming economical. Sources include natural gas and coal conversion, wherein the natural gas and coal are converted to oxygenates and subsequently the oxygenates are converted to light olefins. The product stream from an oxygenates to olefins conversion process needs to be purified to recover the light olefins. Due to the different chemistry from the conversion of petroleum feedstocks to light olefins, the separation and clean-up of the process stream from the oxygenates to olefins conversion process is therefore different.

Improvements in the product separation and recovery can provide for a more pure product stream and a more economical process to recover the purer product stream.

SUMMARY

The present invention is a process for treating the process stream from an MTO process. The heavy hydrocarbons generated in the MTO process present a problem in some of the recycle stages and with subsequent downstream passage of the heavy hydrocarbons. By removing the heavy hydrocarbons, downstream equipment is not fouled by the heavy contaminants.

A first embodiment of the invention is a process for reducing fouling in an MTO process, comprising passing a process stream from an MTO reactor to a quench tower to generate a first overhead stream comprising olefins, and a first bottoms stream comprising waste water; passing the first overhead stream to a product separator unit to generate a second overhead stream comprising olefins and water, a second bottoms stream comprising water, and an intermediate stream comprising water and hydrocarbons; passing the second overhead stream to a product treatment and recovery system; separating the second overhead stream, in compression and separation steps, into a hydrocarbon stream and a water stream; and passing the intermediate stream to a second separation unit.

A second embodiment of the invention is a process for recovering olefins generated in an MTO process, comprising passing a process stream from an MTO reactor to a quench tower to generate a first overhead stream comprising olefins, and a first bottoms stream comprising waste water; passing the first overhead stream to a product separator unit to generate a second overhead stream comprising olefins, a second bottoms stream comprising water, and an intermediate stream comprising water and hydrocarbons; passing the second overhead stream to a product treatment and recovery system; separating the intermediate stream, in a separation step, into a hydrocarbon stream and a water stream; and passing the water stream to a water stripper.

A third embodiment of the invention is a process for recovering olefins from an oxygenate conversion reactor, comprising passing a reactor product stream from an oxygenate to olefins reactor to a quench tower to generate a first waste water stream and a first overhead vapor stream; passing the first vapor overhead stream to a product separator to generate a second waste water stream, a process overhead stream comprising light olefins, and an intermediate stream comprising water and hydrocarbons; passing the process overhead stream to a product compression and cooling unit to generate a compressed product stream and a condensed water stream; passing the compressed product stream to an oxygenate absorber to generate a product stream comprising light olefins and an absorber stream comprising water and oxygenates; and separating the intermediate stream to generate a hydrocarbon stream comprising C4+ hydrocarbons and a third waste water stream.

Other objects, advantages and applications of the present invention will become apparent to those skilled in the art from the following detailed description and drawings.

DETAILED DESCRIPTION

Light olefins can be generated through the conversion of oxygenates to olefins. A common process is the methanol to olefins (MTO) conversion process. The process involves many steps, and includes recycling of streams such as water generated by the MTO process. However, the process generates solid materials and heavy hydrocarbons that can present fouling issues in the process units.

The process includes a product separator, which entailed energy losses in the process of washing and separating water. Difficulty in product separation, as well as difficulty in meeting energy requirements led to improvements in the MTO process. Improvements in the MTO process led to unacceptable levels of contaminants, or heavy components, being carried over to the oxygenate stripper. The subsequent fouling of heat exchangers and downstream devices increased costs, through subsequent energy losses, and need for increased downtime to refurbish fouled devices, in particular heat exchangers. The fouling issues have been found to be the buildup of highly substituted aromatics, such as hexamethyl benzene (HMB) and pentamethyl benzene (PMB).

The invention aims to eliminate the issue of foaming in the oxygenate absorber by removing the source of contaminants that accumulate in the product separator upper section. These contaminants are heavier hydrocarbon components that are carried over from the MTO process. By further separating the pumparound stream and further separating heavier hydrocarbons before they reach the oxygenate absorber, the foaming issues are removed. This is done by preventing or eliminating the buildup of heavies in the product separator top section pumparound.

The present invention provides for maintaining the improvements in energy efficiencies, while removing the components that lead to fouling of downstream units, such as heat exchangers.

Figure 1:
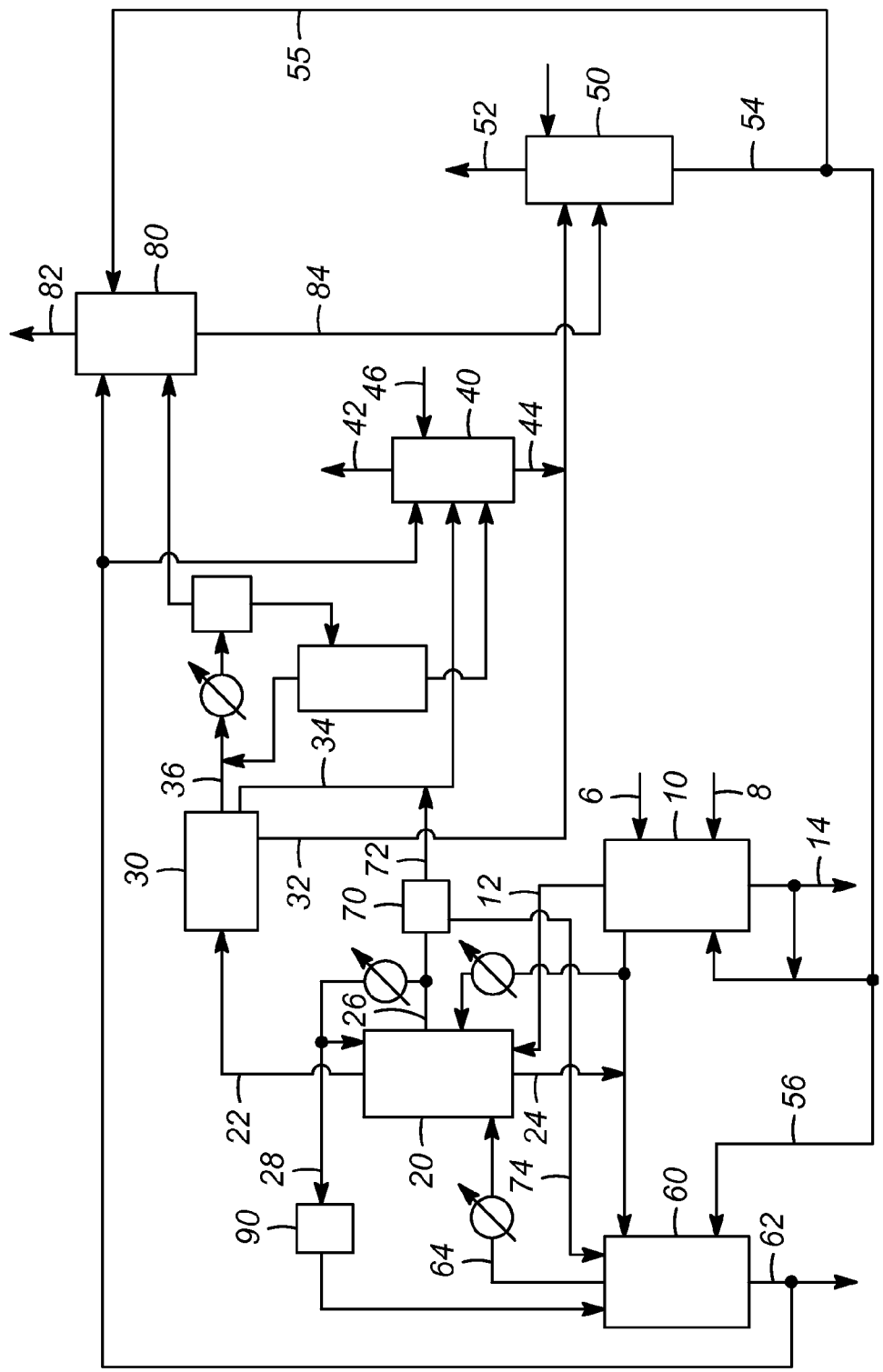
FIG. 1 is a first embodiment of the present invention, with the principal passage of an intermediate stream from the product separator to a water stripper.

The process for recovering light olefins generated in the MTO process is shown in FIG. 1. The process includes passing a process stream 8 from an MTO reactor to a quench tower 10 to generate a first overhead stream 12 and a first bottoms stream 14 comprising waste water. The first overhead stream 12 is passed to a product separator 20 to generate a second overhead stream 22 comprising olefins and water, a second bottoms stream 24 comprising more waste water, and an intermediate stream 26 comprising water and hydrocarbons. The second overhead stream 22 is passed to a product treatment and recovery system to generate a hydrocarbon stream and a water stream. The product treatment and recovery system includes compression 30 and separation steps. The compression with interstage cooling and knockout drums generates a water stream 32 and a hydrocarbon stream 34, and a light hydrocarbon stream 36 comprising light olefins. The process includes passing the intermediate stream 26 to a second separation step to further separate heavy hydrocarbon contaminants from the intermediate stream 26. The light hydrocarbon stream 36 is passed to an oxygenate absorber 80 to remove residual oxygenates and to recycle the recovered oxygenates to the MTO reactor. The oxygenate absorber 80 generates an oxygenate overhead stream 82 comprising light olefins, and an oxygenate bottoms stream 84 comprising water and oxygenates.

In one embodiment, a caustic stream 6 can be passed to the quench tower 10. The addition of caustic will reduce the acidity of the process stream 8 and generate materials that will precipitate and be washed out with the first bottoms stream 14.

The hydrocarbon stream 34 is passed to a wash column 40 to generate a second hydrocarbon stream 42 and a wash stream 44. The wash column 40 includes a feed 46 for a solvent to absorb water from the hydrocarbon stream. The second hydrocarbon stream 42 comprises C4 and heavier hydrocarbons, and the wash stream 44 comprises solvent and water. A preferred solvent is methanol, which can be recycled to the MTO process. Other alcohols and oxygenates that readily absorb water can also be used. The second hydrocarbon stream 42 can be passed to downstream processing units. One such processing unit is an olefin cracking process unit to crack heavier olefins and to further increase the yields of light olefins from the MTO process. The wash stream 44 is passed to an oxygenate stripper 50 to generate an oxygenate stream 52 and a second water stream 54. The oxygenate stream 52 can be recycled to the MTO reactor. The water stream 54 can be used in the quench tower 10 to cool and wash the effluent stream from the MTO reactor. A portion of the water stream 55 can be passed to oxygenate absorber 80 for removing residual oxygenates from the light olefins product stream.

The product separator 20 comprises two parts. A first, or lower, part is where the first overhead stream 12 is passed. The first part removes most of the heat from the first overhead stream 12 and condenses a portion of the water in the first overhead stream to generate the second bottoms stream 24. A portion of the second bottoms stream 24 is cooled and passed to the top of the first part of the product separator 20 and used to perform a cooling and washing function of the first overhead stream 12. A second portion of the second bottoms stream 24 is passed to a water stripper 60 to concentrate the waste water and generate a stream 62 for passing to a water treatment unit. The water stripper 60 generates a water overhead stream 64 for passage to and use in the first part of the product separator 20. A portion of the water stream 56 from the oxygenate stripper 50 can be passed to the water stripper 60.

A vapor stream from the first part of the product separator 20 passed to the second, or upper, part of the product separator 20. A portion of the intermediate stream 26 is cooled and passed as reflux to the top of the second part of the product separator 20. The remainder of the intermediate stream 26 is drawn off and passed to downstream units. It was found that the intermediate stream 26 cannot be passed directly to the oxygenate stripper 50. The intermediate stream 26 can be cooled, and a portion passed as reflux to the top of the second part of the product separator 20, while the remainder 28 as liquid is passed to the water stripper 60. The remainder 28 can be cooled or passed without cooling. This prevents the heavy contaminants from passing to downstream units.

In an embodiment, the remainder 28 of the liquid is passed to a filter system 90 before passing the remainder to the water stripper 60, to remove solids in the intermediate stream.

An alternative is to pass the intermediate to a second separation unit 70. The second separation unit 70 can include a coalescing unit to generate a hydrocarbon stream 72 and a water stream 74. The water stream 74 can be passed to the water stripper 60, and the hydrocarbon stream 72 can be passed to the wash column 40.

In an another alternative, the second separation unit 70 can comprise a settling unit to generate an upper phase comprising hydrocarbons and a lower aqueous phase. The upper phase 72 is drawn off and passed the wash column 40, and the lower phase 74 passed to either the water stripper 60 or the oxygenate stripper 50.

In one embodiment, the separation step can include collecting the intermediate stream, either in the product separator or in a separate vessel. The intermediate stream is then allowed a sufficient holding time to skim off the top layer comprising hydrocarbons and drawing off the bottom layer comprising water.

In a variation, the second separation unit 70 can include passing a clean hydrocarbon stream to the product separator 20 to facilitate the aggregation of hydrocarbons and the separation of the intermediate stream into a hydrocarbon phase and an aqueous phase. The clean hydrocarbon stream would comprise intermediate range hydrocarbons, such as C4 to C6 hydrocarbons and would readily be recovered in the downstream unit such as the water wash column 40.

Figure 2:
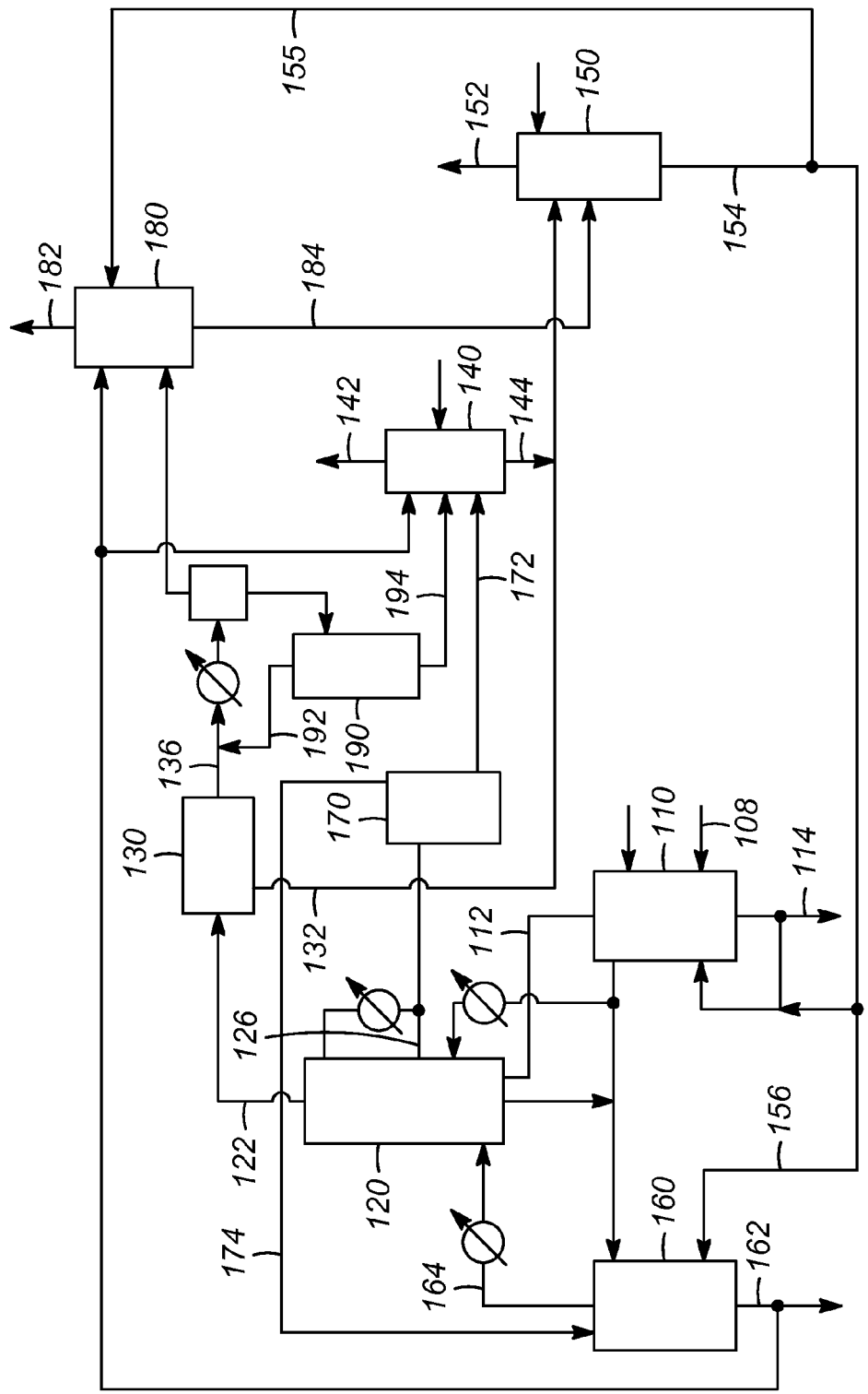
FIG. 2 is a second embodiment of the present invention with the separation of the intermediate stream from the product separator into a water stream and a hydrocarbon stream.

Another embodiment of the present invention, can be seen FIG. 2. The process is for the recovery of olefins generated in a methanol to olefins conversion process. The process includes passing a process stream 108 to a quench tower 110 to generate a first overhead stream 112 comprising olefins and some water, and a first bottoms stream 114 comprising waste water. The first overhead stream 112 is passed to a product separator unit 120 to generate a second overhead stream 122 comprising olefins and some water, a second bottoms stream 124 comprising water and some oxygenates, and an intermediate stream 126 comprising water and hydrocarbons. The second overhead stream 122 is passed to a product treatment and recovery system.

The intermediate stream 126 includes a substantial amount of hydrocarbons comprising C4 and heavier hydrocarbons and water. The intermediate stream 126 is separated into a hydrocarbon stream and a water stream. The separation can be performed in several embodiments. In one embodiment, the separation unit 170 is a settling tank wherein the intermediate stream separates into a hydrocarbon stream 172 and a water stream 174. The hydrocarbon stream 172 is drawn off and passed to a water wash column 140 to generate a hydrocarbon stream 142 comprising C4 and heavier hydrocarbons and a wash column bottoms stream 144 comprising water and oxygenates. The wash column 140 uses water and an alcohol or other oxygenate to draw out residual water and other oxygenates from the hydrocarbon stream 172. A preferred alcohol is methanol. The water stream 174 is drawn off and passed to the water stripper 160 to recover a cleaner water stream for use in the oxygenate absorber 180 and the water wash column 140. The water stripper 160 also generates a water overhead stream 164 for passage to and use in the first part of the product separator 120.

The separation unit 170 can comprise a coalesce for agglomerating small hydrocarbon droplets, or other means known for separating a mixture of hydrocarbons and water.

The product treatment and recovery system includes passing the second overhead stream 122 to a compression and cooling unit 130 to generate a compressed product stream 136 comprising light olefins, and a condensed stream 132 comprising water. The compressed product stream 136 is passed to an oxygenate absorber 180 to generate an oxygenate overhead stream 182 comprising olefins. A portion of the stripped water stream 162 is passed to the oxygenate absorber 180 to remove residual oxygenates from the compressed product stream 136 to generate an oxygenate absorber bottoms stream 184 comprising water and oxygenates. The oxygenate absorber bottoms stream 184 is passed to an oxygenate stripper 150 to generate an oxygenate vapor stream 152, which can be recycled to the MTO reactor, and a second water stream 154. A portion of the water stream 156 from the oxygenate stripper 150 can be passed to the water stripper 160. The water stream 154 can be used in the quench tower 110 to cool and wash the effluent stream from the MTO reactor. A portion of the water stream 155 can be passed to oxygenate absorber 180 for removing residual oxygenates from the light olefins product stream.

The compressed product stream 136 can be further cooled and passed to a dimethyl ether (DME) discharge drum, where condensed DME is collected. The condensed DME is collected and passed to a DME stripper 190 to generate a DME overhead stream 192 comprising olefins and a DME bottoms stream 194 comprising DME and other oxygenates. The DME bottoms stream is passed to the water wash column 140.

The second bottoms stream 124 is passed to the water stripper 160 to generate a stripped water stream 162 to provide recycled water to other units.

Specific Embodiments

While the following is described in conjunction with specific embodiments, it will be understood that this description is intended to illustrate and not limit the scope of the preceding description and the appended claims.

A first embodiment of the invention is a process for reducing fouling in an MTO process, comprising passing a process stream from an MTO reactor to a quench tower to generate a first overhead stream comprising olefins, and a first bottoms stream comprising waste water; passing the first overhead stream to a product separator unit to generate a second overhead stream comprising olefins and water, a second bottoms stream comprising water, and an intermediate stream comprising water and hydrocarbons; passing the second overhead stream to a product treatment and recovery system; separating the second overhead stream, in compression and separation steps, into a hydrocarbon stream and a water stream; and passing the intermediate stream to a second separation unit. An embodiment of the invention is one, any or all of prior embodiments in this paragraph up through the second embodiment in this paragraph further comprising passing the hydrocarbon stream to a wash column to a generate a second hydrocarbon stream comprising C4 and higher hydrocarbons, and a wash stream comprising methanol and water. An embodiment of the invention is one, any or all of prior embodiments in this paragraph up through the second embodiment in this paragraph further comprising passing the second hydrocarbon stream to an olefin cracking process unit. An embodiment of the invention is one, any or all of prior embodiments in this paragraph up through the second embodiment in this paragraph further comprising passing the wash stream to an oxygenate stripper to generate an oxygenate stream and a second water stream. An embodiment of the invention is one, any or all of prior embodiments in this paragraph up through the second embodiment in this paragraph wherein the second separation step comprises passing the intermediate stream to a coalescing unit to generate the hydrocarbon stream and the water stream. An embodiment of the invention is one, any or all of prior embodiments in this paragraph up through the second embodiment in this paragraph wherein the second separation step comprises passing the intermediate stream to a settling unit to generate the hydrocarbon stream and the water stream. An embodiment of the invention is one, any or all of prior embodiments in this paragraph up through the second embodiment in this paragraph wherein the second separation unit generates a second separation water stream and a second separation hydrocarbon stream, further comprising passing the second separation water stream to a water stripper. An embodiment of the invention is one, any or all of prior embodiments in this paragraph up through the second embodiment in this paragraph wherein the second separation unit generates a second separation water stream and a second separation hydrocarbon stream, further comprising passing the second separation water stream to an oxygenate stripper. An embodiment of the invention is one, any or all of prior embodiments in this paragraph up through the second embodiment in this paragraph further comprising passing the intermediate stream to a filtration system. An embodiment of the invention is one, any or all of prior embodiments in this paragraph up through the second embodiment in this paragraph wherein the separation step comprises collecting the intermediate stream from the product separator and skimming the hydrocarbon stream from the top layer of the collected intermediate stream and drawing of the water stream from the bottom of the collected intermediate stream. An embodiment of the invention is one, any or all of prior embodiments in this paragraph up through the second embodiment in this paragraph further comprising adding a clean hydrocarbon stream to the product separator to facilitate the skimming of the hydrocarbons into the hydrocarbon stream.

A second embodiment of the invention is a process for recovering olefins generated in an MTO process, comprising passing a process stream from an MTO reactor to a quench tower to generate a first overhead stream comprising olefins, and a first bottoms stream comprising waste water; passing the first overhead stream to a product separator unit to generate a second overhead stream comprising olefins, a second bottoms stream comprising water, and an intermediate stream comprising water and hydrocarbons; passing the second overhead stream to a product treatment and recovery system; separating the intermediate stream, in a separation step, into a hydrocarbon stream and a water stream; and passing the water stream to a water stripper. An embodiment of the invention is one, any or all of prior embodiments in this paragraph up through the fourth embodiment in this paragraph further comprising passing the second overhead stream to a compression and cooling unit to generate a compressed product stream comprising olefins and a condensed stream comprising water. An embodiment of the invention is one, any or all of prior embodiments in this paragraph up through the fourth embodiment in this paragraph further comprising passing the compressed product stream to an oxygenate absorber to generate an oxygenate free product stream comprising light olefins, and a bottoms stream comprising oxygenates. An embodiment of the invention is one, any or all of prior embodiments in this paragraph up through the fourth embodiment in this paragraph wherein the intermediate stream is passed to a separation unit, and wherein the separation unit comprises a coalescing unit to generate the hydrocarbon stream and the water stream. An embodiment of the invention is one, any or all of prior embodiments in this paragraph up through the fourth embodiment in this paragraph further comprising passing the hydrocarbon stream to a water wash column; and passing a methanol stream to the water wash column to generate a C4+ hydrocarbon process stream and a water and methanol stream.

A third embodiment of the invention is a process for recovering olefins from an oxygenate conversion reactor, comprising passing a reactor product stream from an oxygenate to olefins reactor to a quench tower to generate a first waste water stream and a first overhead vapor stream; passing the first vapor overhead stream to a product separator to generate a second waste water stream, a process overhead stream comprising light olefins, and an intermediate stream comprising water and hydrocarbons; passing the process overhead stream to a product compression and cooling unit to generate a compressed product stream and a condensed water stream; passing the compressed product stream to an oxygenate absorber to generate a product stream comprising light olefins and an absorber stream comprising water and oxygenates; and separating the intermediate stream to generate a hydrocarbon stream comprising C4+ hydrocarbons and a third waste water stream. An embodiment of the invention is one, any or all of prior embodiments in this paragraph up through the sixth embodiment in this paragraph further comprising passing the second waste water stream to a water stripper. An embodiment of the invention is one, any or all of prior embodiments in this paragraph up through the sixth embodiment in this paragraph further comprising passing the third waste water stream to a water stripper An embodiment of the invention is one, any or all of prior embodiments in this paragraph up through the sixth embodiment in this paragraph further comprising passing the hydrocarbon stream to a water wash column to generate a C4+ hydrocarbon stream and a wash water stream comprising methanol and water.

While the invention has been described with what are presently considered the preferred embodiments, it is to be understood that the invention is not limited to the disclosed embodiments, but it is intended to cover various modifications and equivalent arrangements included within the scope of the appended claims.

What is claimed is:

1. A process for reducing fouling in an MTO process, comprising:
   passing a product effluent stream comprising olefins, solid materials, and highly substituted aromatic hydrocarbons including hexamethylbenzene and pentamethyl benzene from an MTO reactor to a quench tower to generate a first overhead stream comprising olefins and said highly substituted aromatics, and a first bottoms stream comprising waste water;
   passing the first overhead stream to a product separator unit to generate a second overhead stream comprising olefins and water, a second bottoms stream comprising waste water, and an intermediate stream comprising water and highly substituted aromatic hydrocarbons;
   passing the second overhead stream to a product treatment and recovery system to separate the second overhead stream, in compression and separation steps, into a hydrocarbon stream and a water stream and a light hydrocarbon stream comprising olefins;
   passing the water stream from the product treatment and recovery system to an oxygenate stripper;
   cooling a portion of the intermediate stream and passing a portion of the cooled portion of the intermediate stream as reflux to the top of the product separator unit and the remainder to a water stripper to generate a water overhead stream for use in the product separator unit and a water bottom stream for passing to a water treatment unit;
   passing another portion of the intermediate stream to a second separation unit to generate a hydrocarbon stream containing highly substituted aromatic hydrocarbons a second bottoms stream comprising waste water;
   passing the first bottoms stream comprising waste water, second bottoms stream comprising waste water, and second bottoms stream comprising waste water to the water stripper;
   passing the hydrocarbon stream and the stream containing highly substituted aromatic hydrocarbons to wash column to generate and a washed hydrocarbon stream comprising C4 and higher hydrocarbons and a wash stream comprising methanol and water; and
   passing the washed hydrocarbon stream to an olefin cracking process.

2. The process of claim 1 further comprising passing the wash stream to an oxygenate stripper to generate an oxygenate stream and a second water stream.

3. The process of claim 1 wherein the second separation unit is a coalescing unit.

4. The process of claim 1 wherein the second separation unit is a settling unit.

5. The process of claim 1 further comprising passing the intermediate stream to a filtration system.

6. The process of claim 1 wherein the separation step comprises collecting the intermediate stream from the product separator and skimming the hydrocarbon stream from the top layer of the collected intermediate stream and drawing of the water stream from the bottom of the collected intermediate stream.

7. The process of claim 6 further comprising adding a clean hydrocarbon stream to the product separator to facilitate the skimming of the hydrocarbons into the hydrocarbon stream.

\* \* \* \* \*